US007776364B2

(12) United States Patent
Thierman

(10) Patent No.: US 7,776,364 B2
(45) Date of Patent: Aug. 17, 2010

(54) NON-SURGICAL METHOD FOR TREATING CATARACTS IN MAMMALS INCLUDING MAN

(75) Inventor: Mark Thierman, Tucson, AZ (US)

(73) Assignee: Advanced Scientific, LLC, Washington Crossing, PA (US)

( * ) Notice: Subject to any disclaimer, the term of this patent is extended or adjusted under 35 U.S.C. 154(b) by 707 days.

(21) Appl. No.: 11/388,882

(22) Filed: Mar. 24, 2006

(65) Prior Publication Data

US 2007/0224294 A1 Sep. 27, 2007

(51) Int. Cl.
*A61K 38/05* (2006.01)
*A61K 31/525* (2006.01)

(52) U.S. Cl. ........................ 424/717; 514/18; 514/250; 514/546

(58) Field of Classification Search .................. 424/717
See application file for complete search history.

(56) References Cited

U.S. PATENT DOCUMENTS

| | | | | |
|---|---|---|---|---|
| 5,110,796 | A * | 5/1992 | Itoi et al. | 514/18 |
| 6,010,699 | A * | 1/2000 | Honda et al. | 424/94.63 |
| 6,194,457 | B1 * | 2/2001 | Braswell et al. | 514/547 |
| 2005/0112113 | A1 * | 5/2005 | Till et al. | 424/94.1 |

FOREIGN PATENT DOCUMENTS

| | | | |
|---|---|---|---|
| WO | WO 95/10294 | * | 4/1995 |
| WO | WO95/10294 | A1 | 4/1995 |
| WO | WO2004/028536 | A1 | 4/2004 |
| WO | WO2004/064866 | A1 | 8/2004 |

OTHER PUBLICATIONS

Rathbun (Age-related cysteine uptake as rate-limiting in glutathione synthesis and glutathione half-life in the cultured human lens. Exp Eye Res. Aug. 1991;53(2):205-12.*

U.S. Appl. No. 60/414,357, M.A. Babizhayev.

Mark A Babizhayev et al, L-Carnosine (β-alanyl-L-histidine) and carcinine . . . , *Biochem J.* (1994), v.304, p. 509 (Great Britain).

Venkat N. Reddy et al., "Glutathione Peroxidase-1 Deficiency . . . ," 42 Inv. Opth. & Vis. Sci. 3247 (2001) (USA).

F. Tessier et al., "Decrease In Vitamin C . . . ," 68 Int. J. Vitam. Nutr. Res. 309 (1998) (USA) (Abstract Only).

WB Rathbun et al., "Age-Related Cysteine Uptake . . . ," 53 Exp. Eye Res. 205 (1991) (Abstract only).

Babizhayev et al., "N-Acetylcarnosine, A Natural Histidine . . . ," 22 Peptides 979 (2001).

Babizhayev et al., "Efficacy of N-Acetylcarnosine . . . ," 3 Drugs R&D 88 (2002).

Babizhayev, "Failure to Withstand Oxidative Stress . . . ," 1315 Biochim. Biophys. Acta 87 (1996).

Babizhayev, "Rejuvenation of Visual Functions . . . ," 7 Rejuven. Res. 186 (2004).

I.F. Maichuk et al., "Development of Carnosine Eyedrops . . . ," 113 Vestnik Ofthalmologii 27 (Moscow, 1997) (in Russian, with Abstract in English).

Frank J. Giblin, "Glutathione: A Vital Lens Anti-Oxidant," 16 J. Ocular Pharm. Thera. 121 (2000).

Mark A. Babizhayev et al., "Nα-Acetylcarnosine Is a Drug of L-Carnosine . . . ," 254 Clin. Chem Acta 1 (1996).

M.A.Babizhayev et al., "The Natural Histidine-Containing Dipeptide . . . ," 65 Biochem 588 (2000) (Moscow).

* cited by examiner

*Primary Examiner*—Jake M. Vu
(74) *Attorney, Agent, or Firm*—Pharmaceutical Patent Attorneys, LLC

(57) ABSTRACT

An anti-oxidant cocktail demonstrated efficacious in the treatment of avian and mammalian cataracts, useful for veterinary and human use as a veterinary or human pharmaceutical (to cure existing cataracts) or as a dietary supplement (to maintain a healthy, non-diseased state).

20 Claims, No Drawings

NON-SURGICAL METHOD FOR TREATING CATARACTS IN MAMMALS INCLUDING MAN

GOVERNMENT INTEREST

None

RELATED APPLICATIONS

None

BACKGROUND

For optimal vision, ocular lens proteins should be translucent. Senile cataracts are generally thought to be the result of oxidation damage to expressed DNA sequences that encode for ocular lens proteins. This oxidation damage is generally thought to be caused by free radicals in vivo. As a result of free radical oxidation, the coding DNA sequence is transcribed and translated into polypeptide which is not completely transparent. Eventually this accumulation of errors develops into what is medically recognized as a cataract.

The eye protects its DNA from damage with numerous antioxidant systems. In the development of a senile cataract, I infer that more than one of these antioxidants systems have been compromised or damaged. This injury results in an accrual of damage at a faster rate than repair can take place in the eye.

The prior art generally focuses on one or two components for eye care. Thus, previous attempts to treat senile cataracts have focused on single components such as L-Carnosine or N-Acetyl-L-Carnosine as antioxidants. For example, Mark A. BABIZHAYEV, *Method for Topical Treatment of Eye Disease*, Published PCT Application No. WO 2004/28536, teaches the use of L-carnosine and Acetylhistidine for cataracts. Alternatively, Mark A. BABIZHAYEV et 20 al., *N-Acetylcarnosine Is A Prodrug Of L-Carnosine In Opthalamic Application,* 254 CLINICA CHIMICA ACTA 1 (1995), Mark A. BABIZHAYEV et al., *N-Acetylcarnosine, A Natural Histidine-Containing Dipeptide . . . ,* 22 PEPTIDES 979 (2001), and Mark A. BABIZHAYEV, *Pharmaceutical Compositions Containing N-acetylcarnosine*, Published PCT Application No. WO 1995/10294, teaches to use N-acetylcarnosine for the treatment of cataracts. These types of eye drop treatments have met with only very limited success because no single antioxidant developed previously has been powerful enough to compensate for all of the compromised systems in the eye.

In contrast, I reasoned that a multi-faceted, systems-based approach to supplementing the major antioxidant systems in the eye might be more efficacious. As a result, I focused my research on a multifaceted approach that incorporates a formula comprising numerous antioxidants, each designed to support a specific and crucial failing antioxidant system in the eye. My result is a complex system which is far more effective that a single-ingredient approach, since it is able to slow or stop damage on a much wider scale that of a single component approach.

My invention constitutes a new non-surgical method for treating common eyesight obstructions, i.e., cataracts & lenticular sclerosis, which is very broad in nature. It generally constitutes the administration of a specially formulated antioxidant eye drop topically administered three times per day. The eye drop utilizes a systems-type approach to relieving oxidant strain on the eye. Previous art has addressed only one or two antioxidant systems which are insufficient to allow the eye to repair the oxidative damage accrued resulting in the formation of the cataract or vision obstruction. A comprehensive systems approach, however, relieves oxidative strain on the eye in a manner sufficient to allow to eye to repair itself (i.e., dissolve the cataract or lenticular sclerosis) in approximately 70 days in human subjects. This holds true for cataracts so severe that the only other treatment option is laser surgery. This approach is analogous to kidney dialyzation which reduces the normal work load on the kidney, thus allowing the kidney to repair the damage to itself to some degree.

My invention is composed of numerous sophisticated antioxidants which work in concert utilizing a "systems" approach. Some of these antioxidants are so unusual that they must be custom synthesized (i.e. synthetically produced in a laboratory) before being formulated into the eye drop in the correct proportions. These antioxidants, when placed in the eye in a liquid solution form, act together, and possibly synergistically, to supplement the various natural eye antioxidant systems, which would be normally produced in sufficient quantities to protect the eye from genetic damage and error.

However, as a mammal ages, it often becomes incapable of producing sufficient quantities of these antioxidants—due to free radical damage—to protect the highly conserved part of the genome which specifies these crucial eye antioxidants. This results in the formation of aberrant proteins, which cloud the lens, ultimately forming a cataract. By exogenously administering these antioxidants and other nutrients, the eye is temporarily relieved of the burden of synthesizing these antioxidants and can devote its limited energy to repairing the cataract. (See analogy to dialysis, supra). Depending upon the synthetic methods used and the concentration of the antioxidants used in the formula, 15 milliliters (approximately a two month supply of the eye drop) can usually have an obvious positive effect on a human in 2-3 months. The steps involved in manufacturing the invention are the synthesis/purchase of the necessary ingredients, the formulation of these components into a liquid solution, and then the sterilization of this bulk solution through a 0.2-micron filter for sterilization. The sterile bulk solution can then be packaged according to retail needs/requirements.

The efficacy and superiority of my systems-based approach is supported by actual treatment results, which distinguishes my eye drop discovery from other previous attempts to reduce oxidative damage in the eye that allows the eye to repair the cataract. Currently, there are no known disadvantages or limitations of my product.

DETAILED DESCRIPTION

Like the prior art, my product includes N-acetylcarnosine. N-acetylcarnosine is a powerful antioxidant. It provides longer-term protection against free radicals than Carnosine due to its longer in vivo residence and activity time in the cells, before being ultimately metabolized into Carnosine itself. In contrast to the prior art, however, I add several other components to make a synergistically more effective mixture.

One component is L-Carnosine. L-Carnosine is known in the art to be significantly less stable in vivo than is N-Acetylcarnosine. Thus, one might expect L-Carnosine to add little or no benefit to N-Acetylcarnosine. I have found, however, that adding L-Carnosine provides an immediate neutralization of already-existing free radicals in vivo, an immediate neutralization which N-Acetylcarnosine, due to its greater thermodynamic stability, effects much more slowly. Carnosine has been approved by the Russian Federation as 5% ophthalmic solution for use in eye drops as and adjunct therapy for treating corneal ulcers, herpes virus infections, bacterial infections, and dry keratoconjuctivitis. See generally, Maichuk, IuF; 113 VESTNIK 20 OFTALMOLOGII 27 (1997).

Another component is L-Glutathione. In a healthy lens, this may be the single most important antioxidant. In vivo, L-Glutathione becomes oxidized (thus absorbing free radicals). Once it is oxidized, however, it cannot accept further free radicals unless it is reduced again. For a general background on glutathione and its potential as a lens antioxidant, see Giblin, Frank J., 16(2) J. OCULAR PHARMA. AND THERAPEUTICS_(2000).

Thus, I also use L-cysteine. The body uses L-cysteine to reduces the L-Glutathione which becomes oxidized in vivo in the eye. This enables the L-Glutathione to effect several oxidation-reduction cycles. Cysteine eye concentration is a known rate limiting factor in glutathione ocular synthesis. See Rathbun, W. B.; 53 EXPER. EYE RES. 205 (1991).

I prefer to provide the L-cysteine in the form of a water-soluble precursor such as the salt cysteine ascorbate, which provides a water stable source of both L-cysteine and vitamin C, both important water-soluble antioxidants. The stability of aqueous cysteine ascorbate has not been completely described, although it appears to be the most stable of all amino ascorbates in water ranging from ambient temperature to above boiling. See Lotti, B., 27 FARMACO 275 (1972). Vitamin C is known in the art to be an excellent absorber of UV radiation between 280-310 nm. See Brubaker, Richard F., 41 INVEST. OPHTHAL. & VISUAL SCI. 1681 (2000). Vitamin C is known to be highly concentrated in both the aqueous humor and the corneal epithelium of the eye, even in the absence of any topical nutritional supplementation. See id. Thus, one of skill in the art might believe it superfluous to add topically add additional vitamin C. Cf. Tessier, F., 68 INDIAN J. OF NUTRIT. RES. 309 (1998). I to the contrary believe topical vitamin C and L-Cysteine quite beneficial because together, as a salt, they stabilize the L-cysteine and Ascorbic acid in the aqueous solution without the use of minerals, which catalyze free radical reactions. Aqueous stabilization of these compounds has long been an object of prior art. I also prefer to add other nutrients, to support the repair of the damaged lens tissues, etc. . . . For example, I prefer to include riboflavin because it plays a critical role in the synthesis of glutathione reductase. See Beatty, Steven, 45 *Survey of Ophthamology* 115 (2000).

As another example, I prefer to include taurine, because in the eye, taurine concentrations are higher than that of any other amino acid (in a healthy eye, ranging from about 50 to 70 mM). See Lima, L., 24 NEUROCHEM. RES. 1133 (1999). Additionally, taurine may act to actually regenerate nerve cells such as neurites in the optic nerve. Id.

As with any ophthalmic, the pH of the final product should be buffered and adjusted to an appropriate pH. While different buffers may be suitable, I prefer to use sodium bicarbonate, because a bicarbonate electrolyte composition which is near that of human tears appears to promote healing of the corneal epithelium. See Lopez, Bernard D. 12 CORNEA 115 (1993). In addition, the solution must be kept aprotic (basic, i.e. pH above 7.0) to remain stable. The use of sodium bicarbonate as a buffer accomplishes this naturally.

I prefer to add propylene glycol in the range of 0.2%-1.0%, or another acceptable ophthalmic lubricant. Propylene glycol is an F.D.A.-approved ingredient for ophthalmic use as a lubricant. See 21 C.F.R. §349.12(d)(5). Under ordinary conditions, propylene glycol is stable; however, mixing it with water may accelerate its tendency towards oxidation at higher temperatures. Consequently, it is advisable to add antioxidants to prevent any undesirable oxidation of the propylene glycol. In addition, the product should be stored in a cool (70-80° F.), but not cold (i.e. as in a refrigerator), environment as chilling the solution may cause precipitation/crystallization of certain antioxidants.

I also prefer to include polysorbate-80 in the range of 0.20%-1.0% because it is more chemically stable than is propylene glycol. Use of this in conjunction with propylene glycol increases the chance of successfully treating ocular xerosis in a greater percentage of users than relying on only one or the other ingredient. Further, it is F.D.A.-approved for ophthalmic use as a lubricant. See 21 C.F.R. §349.12(d)(4).

I prefer to use pharmaceutical-grade compounds to make my preparation; most of these are commercially available. At the present time, N-Acetyl-L-Carnosine (CAS No. [56353-15-2]) is not commercially available; it may, however, be synthesized as is known in the art. Commercially-procured Carnosine used to require purification to remove the hydrazine contaminant generated during its synthesis. This is no longer necessary as manufacturers have recognized and corrected the problem. See Decker, E. A., 65 BIOCHEMISTRY 766 (2000); Zhou, Shengying, 261 ANALYTICAL BIOCHEMISTRY 79 (1998).

EXAMPLE 1

At this writing, I prefer the following preparation. To make 20 liters, use:

1. N-Acetyl-L-Carnosine-CAS [56353-15-2] 5
   Use 2.0% solution=400 grams/20 liters (w/v).
2. Carnosine-CAS [305-84-0]
   Use 2.0% solution=400 grams/20 liters (w/v).
3. Glutathione-CAS [70-18-8]
   Use 2.0% solution=400 grams/20 liters (w/v). 10
4. Cysteine Ascorbate-CAS [35412-64-7]
   Use 2.0% solution=400 grams/20 liters (w/v).
5. Riboflavin Monophosphate-CAS [146-17-8]
   Use 0.5% solution=100 grams/20 liters (w/v).
6. Taurine-CAS [107-35-7]
   Use 1.0% solution=200 grams/20 liters (w/v).
7. Sodium Bicarbonate-CAS [144-55-8]
   Use approximately ~86-93 grams/20 liters (adjust final solution pH to ~7.2)(w/v).
8. Propylene Glycol-CAS [57-55-6]
   Use 0.20% solution=38.7 ml/20 liters. 20
9. Polysorbate 80-CAS [9005-65-6]
   Use 0.20% solution=300 grams/150 liters=283 ml/150 liters=37.8 ml/20 liters.

Formulation Procedure.

1. For 20-liter Batch Scale:

a. Weigh/measure out appropriate amounts of ingredients 1-9. Note: Use initially only 5-6 grams of sodium bicarbonate, then later adjust final pH of final solution to approximately 7.2-7.4 by using additional sodium bicarbonate (total sodium bicarbonate=~8.5-9.5 grams total/20 liters). b. Dissolve ingredients #1-#8 in 15 liters of distilled water at room temperature (~20° C.). Note: This may require some form of agitation to effect complete solution of all ingredients.

c. Dissolve ingredient 9 (with stirring or shaking) in approximately one liter of distilled water previously heated to ~50° C.

d. Combine solution-containing ingredients 1-8 with solution containing ingredient 9. Dilute to final volume of 20 liters with additional distilled water and thoroughly agitate to create a homogeneous solution.

e. Adjust pH of final 20 liter solution to ~7.2-7.4 by portion wise addition of remaining sodium bicarbonate. Note: Thoroughly agitate the solution after addition of each portion in order to accurately measure pH until 20-liter solution is slightly acidic (pH ~7.2-7.4).

f. Filter final 20 liter solution through 0.2 m cartridge filter system to effect sterilization of final solution.

EXAMPLE 2

Clinical Study Results (Non-Surgical Sight Improvement/Reduction of Eye Cataracts).

The Assignee initiated a veterinary private practice and university based objective study designed to evaluate the efficacy of my preparation on mammalian and avian eye cataracts. The study was conducted in the USA, Canada and the United Kingdom. The test subjects were predominately dogs, a species that has a particularly high incidence of cataracts. Initial study results are as follows:

Pets with mature well-established cataracts and who had compliant type owners were selected for the study. Owners were instructed to apply one drop three times daily in each treatment eye. Owners were requested to return to their veterinarian at four, six and eight weeks after starting the test period, to enable the attending veterinarian to evaluate the test subject. My preparation was tested on three species; dog, parrot, and cat.

Our results show that my preparation is effective after only four weeks of use. Of 38 dogs (age ranging from 4 to 18 years of age) tested, 31 achieved a positive outcome. Of one parrot tested, one achieved a positive outcome. Of one cat tested, one achieved a positive outcome. Table 1 provides examples of comments recorded by the veterinarians attending to the dogs.

| BREED | AGE | COMMENTS |
|---|---|---|
| Yorkshire Terrier | 12 | A little clearing pin hole is forming in the cataract, |
| Lab/Pit | 12 | Prior to treatment the cataract in both eyes covered 55% of the eye. 1. Both eye cataracts reduced 40% coverage 4-weeks 2. Both eye cataracts reduced to 30-35% coverage at 6-weeks. Marbling minimizing noted with a few holes forming in the cataract in both eyes 3. Both eye cataracts reduced to 30% coverage at 8-weeks and noticing well-defined edge of the cataracts. Lenses have cleared up enough that no real bubbling or crack effect is visible. OWNER VERY HAPPY WITH RESULTS. |
| Golden Retriever | 13 | Cataract coverage prior to treatment: 80-85% Cataract coverage at 4-weeks: 60-65% both eyes. |
| French Bulldog | 5 | Haze of cataract reduced 40% eye one Haze of cataract reduced 35% eye two The cracks in the lens of both eyes are greatly reduced: SUBJECT PROGRESSING WELL |
| Maltese | 13 | Haze of cataract reduced from 70% prior to treatment to 60% in both eyes. Cracks in the cataract in both eyes has been reduced by 30% Owner reports vision improved, |
| Shi Tzu | N/A | Eye one: Pre-treatment 100% lens coverage Eye one: 4-weeks 50% improvement in lens coverage, crystallization is reduced and opacity is improved, Eye two: crystallization reduced 5-10% |
| Lab | 4 | 1. Clearing of the cortex (cataract) noted at 4-wks 2. Continued clearing noted at 6-wks 3. At 8-weeks the cortex in both eyes are definitely much clearer, still some cataract visible. |
| Shi Tzu | 10 | Eye one: 25% reduction in size of cataract Eye two: 25% reduction in size of cataract |
| Feline | 15 | 4-week check up both eyes much improved 6-week checkup 1. RIGHT EYE NOW CLEAR OF CATARACT 2. LEFT EYE-SHOWS A 25% IMPROVEMENT IN CATARACT SIZE |
| Wire Fox Terrier | 6 | Visual improvement noted in one eye At six-week examination slight improvement is noted in the other eye. |
| Miniature Pinscher | 8 | Eye One: Cataract not in evidence at 4-wks Eye Two: 30% reduction in cataract |
| Golden Retriever | 6 | Eye One: 5-10% improvement in reduction Eye Two: 25% improvement in reduction |
| Parrot | 27 | This patient is virtually blind in both eyes due to cataract formation due to trauma. Was scheduled for cataract surgery. One eye is under testing and after four weeks the owner has seen enough progress that surgery has been delayed or cancelled. Owner comments that the long time sightless test eye now is showing an improvement in opacity and that the subject is now responding to sight movement were there was none previously, |
| Corgi | 15 | After eight weeks of application the Cortex (perimeter) of the sight obstructing in both eyes are definitely clearing. Owner reports that the patient can catch its treats again. |

-continued

| BREED | AGE | COMMENTS |
| --- | --- | --- |
| Min-Picher | 18 | Four Week Report:<br>1. Right Eye: Small cracks and holes are appearing in the cataract as it breaks up and eye does not bulge as much as it did before treatment<br>2. Left Eye: Cataract appears 5-10% smaller in diameter and seems less opaque and clearer. Owner reports his dog can see better. |
| Standard Poodle | 7 | Before treatment patient had 40%-50% vision covered by a 25% cataract in both eyes.<br>1. After two weeks of treatment patient's cataracts in both eyes have been reduced to 15% coverage. |
| Poodle | 17.5 | Right Eye 85% cataract coverage and very opaque<br>Left Eye 70% cataract coverage and less opaque than the right eye.<br>AT FOUR WEEKS:<br>1. RIGHT EYE: No change noted<br>2. LEFT EYE: Less opaqueness on the cataract and the owner reports the dog is now less startled by movement in front of her as she was initially |
| Spaniel Mix | 13 | PRIOR TO TREATMENT:<br>1. Right Eye 100% coverage, very white and opaque completely blind.<br>2. Left Eye 80% coverage with medium opaqueness.<br>AT FOUR WEEKS:<br>1. Right Eye: No change noted<br>2. Left Eye: Less opaque no change in diameter<br>AT SIX WEEKS:<br>1. Right Eye: Cracks appearing in the cataract<br>2. Left Eye: Cracks appearing in the cataract. Opaqueness diminished and cataract is smaller in diameter 10% improvement. Owner reports that patient is more active and seems to be seeing objects now where he could not before. |

Test Subject 27 Year Old Parrot

The Test Subject was virtually blind in both eyes due to cataract formations due to traumas. The Test Subject was scheduled for cataract surgery. One eye was tested for responsiveness to my preparation. After four weeks of treatment, the owner has seen enough improvement in the cataracts that surgery has been cancelled. In addition, the owner observed that the long-time sightless test eye now is showing an improvement in opacity and that the test subject is now responding to sight movement, where there was no response previously.

A veterinarian reviewing these photographs concluded, "The lenticular opacity is not very visible on the week 0 photos, however, what I notice is that the sclera, although still hyperemic, appears somewhat better organized around the margins of the iris on the week 4-5 photo, and at least you can see the lenticular opacity on the week 4 photo."

In addition to an observable clarification in lens transparency, various pet owners have reported that within just a few weeks of treatment they have noticed changes in their animal's behavior, including:

1. More Activity and Mobility
2. Increased Appetite
3. Improved mood and a happier disposition As with any study, patient compliance is an issue to consider both in the application of the eye drops as prescribed, and in reporting for progress analysis to the attending veterinarian (or physician, for human use). Every reasonable effort has been made to have the test subjects selected to meet acceptable standards. All patients selected had mature, well-formed cataracts that in many cases had taken years to form.

These results indicate that my product will be highly effective in treating already-existing cataracts as well as in preventing new cataracts (i.e., useful in preventive treatment, to maintain a healthy normal state).

As it now stands, the present formula is generally capable of either completely eliminating surgically severe cataracts in humans in 60-90 days, or at least reducing their severity so that surgery is no longer required. When using this same human formula in mammals such as canines, a longer period of treatment is required for similar results. This may be due to the fact that canines simply do not have as sophisticated reparative mechanisms in the eye as do humans, or it may also be that the present formula may need to be optimized for each mammalian species it is intended to treat. For comparison purposes, the only other semi-effective eye drop purported to treat cataracts requires at least 6 months to show even a marginal improvement in reducing the cataract, and in some cases no benefit can be ascertained even after 6 months of treatment (see Babizhayev, WO 2004/028536), whereas there have been no treatment failures utilizing the present formula of invention.

Therefore, a utility of my invention is to provide a highly effective, extremely safe, and cost effective alternative to the only other treatment option (laser surgery) for severe cataracts in mammals (especially man). In addition, my invention can be used as a prophylactic to prevent the formation of cataracts in mammals such as canines, felines reptiles etc., but especially man.

Presently, mammalian cataracts are treatable primarily by laser surgery, which is not only expensive (approximately $2,500.00), but poses significant side effects including the possibility of blindness. Lens transplants also may be effective but are also equally expensive and heal very slowly. The present invention offers a highly effective (no treatment failures in preliminary testing) and at a cost of less than $160.00 per treatment period.

In the claims appended, I use the term "comprising" to allow for additional matter. Thus, the singular encompasses the plural (e.g., "composition comprising a salt" reads on compositions including one—and possibly more—salts). I intend the legal coverage of this patent to be defined by the claims, rather than the abstract or specification (this is what claims are for).

I claim:

1. A composition of matter comprising: N-Acetyl-L-Carnosine, Carnosine, Glutathione and Cysteine, said N-Acetyl-L-Carnosine, Carnosine, Glutathione and Cysteine present in amounts which, when taken together, are effective to chemically reduce the amount of free radicals which would normally be found in vivo in the eye.

2. The composition of claim 1, said N-Acetyl-L-Carnosine, Carnosine, Glutathione and Cysteine present in a ratio of approximately 1:1:1:1.

3. The composition of claim 1, further comprising a buffer.

4. The composition of claim 3, said buffer comprising sodium bicarbonate.

5. The composition of claim 1, further comprising a lubricant.

6. The composition of claim 5, said lubricant selected from the group consisting of propylene glycol and polysorbate-80.

7. The composition of claim 6, said lubricant comprising propylene glycol and polysorbate-80.

8. The composition of claim 1, further comprising taurine.

9. The composition of claim 1, further comprising riboflavin monophosphate.

10. The composition of claim 8, further comprising riboflavin monophosphate.

11. A method comprising administering the composition of claim 1 to an eye.

12. A method comprising administering the composition of claim 2 to an eye.

13. A method comprising administering the composition of claim 3 to an eye.

14. A method comprising administering the composition of claim 4 to an eye.

15. A method comprising administering the composition of claim 5 to an eye.

16. A method comprising administering the composition of claim 6 to an eye.

17. A method comprising administering the composition of claim 7 to an eye.

18. A method comprising administering the composition of claim 8 to an eye.

19. A method comprising administering the composition of claim 9 to an eye.

20. A method comprising administering the composition of claim 10 to an eye.

* * * * *